(12) United States Patent
Horiguchi

(10) Patent No.: US 8,216,191 B2
(45) Date of Patent: Jul. 10, 2012

(54) HEMODIALYSIS USE ADJUNCTIVE DEVICE

(76) Inventor: Sachio Horiguchi, Hyogo (JP)

( * ) Notice: Subject to any disclaimer, the term of this patent is extended or adjusted under 35 U.S.C. 154(b) by 293 days.

(21) Appl. No.: 11/936,287

(22) Filed: Nov. 7, 2007

(65) Prior Publication Data

US 2008/0132849 A1 Jun. 5, 2008

(30) Foreign Application Priority Data

Dec. 5, 2006 (JP) ................................. 2006-328062

(51) Int. Cl.
*A61M 1/00* (2006.01)
(52) U.S. Cl. ........................................ 604/175
(58) Field of Classification Search .......... 604/246, 604/157, 175, 207, 284
See application file for complete search history.

(56) References Cited

U.S. PATENT DOCUMENTS

| | | | |
|---|---|---|---|
| 4,108,173 A | | 8/1978 | Slivenko et al. |
| 4,417,888 A | * | 11/1983 | Cosentino et al. ............ 604/175 |
| 5,755,779 A | * | 5/1998 | Horiguchi ..................... 606/157 |
| 6,524,273 B2 | * | 2/2003 | Kawamura ................. 604/93.01 |

* cited by examiner

*Primary Examiner* — Kevin C. Sirmons
*Assistant Examiner* — Brandy C Scott
(74) *Attorney, Agent, or Firm* — Studebaker & Brackett PC; Donald R. Studebaker

(57) ABSTRACT

A hemodialysis use adjunctive device comprises an artificial blood vessel to be transplanted in the body at a location between an artery and a vein, a T-shaped tubular body comprising a straight tube portion and a stem portion and interposed in the artificial blood vessel, and an access tube provided at one end portion thereof with a jack having a pair of needles. A throttling unit is provided in the straight tube portion and is arranged so that it can be located between the pair of needles of the jack projecting from the stem portion to the straight tube portion when the jack of the access tube is connected to the stem portion of the tubular body. This arrangement can provide the result that while hemodialysis can be performed properly, internal membrane thickening of the vein and the resulting stricture or obstruction of the same can be prevented.

8 Claims, 4 Drawing Sheets

HEMODIALYSIS USE ADJUNCTIVE DEVICE

BACKGROUND OF THE INVENTION

The present invention relates to a hemodialysis use adjunctive device partly implanted in the body for hemodialysis.

As disclosed in the description and drawings of U.S. Pat. No. 4,417,888, for example, this type of hemodialysis use adjunctive device is generally known which comprises an artificial blood vessel to be transplanted in the body at a location between an artery and a vein, such as, for example, between a brachial artery and a brachial vein, a T-shaped tubular body comprising a straight tube portion and a stem portion and interposed in the artificial blood vessel, and an access tube provided at one end thereof with a jack having a pair of needles and is used for hemodialysis by performing the step that the tubular body is transplanted in the human body together with the artificial blood vessel in the state of the stem portion being exposed at its top end portion from the body and then, at the time of hemodialysis, the jack of the access tube is connected to the stem portion of the tubular body and the other end portion of the access tube is connected to a hemodialysis machine.

However, this conventional type one has the problem that when the artificial blood vessel and the tubular body, serving as the hemodialysis use adjunctive device, are transplanted in the body, a blood flow is increased in the vein into which the blood flows through the artificial blood vessel, so that an increased hydrodynamic stress (or rather, an increased shearing stress) acts on the blood vessel wall of the vein, from which internal membrane thickening results, then ending up in stricture or obstruction. This problem is caused not only when the hemodialysis use adjunctive device is transplanted in the body but also when an anastomosis between an artery and a vein is made to enlarge the vein for the facilitation of the hemodialysis.

In order to solve this problem, the inventor of this application previously proposed that a blood stream adjuster having a throttling portion for controlling the blood stream is fitted in the artificial blood vessel (Cf. Description and drawings of U.S. Pat. No. 5,755,779). However, since it is necessary for the blood flow of the order of 60-600 ml/min to flow through the artificial blood vessel of the hemodialysis use adjunctive device during the hemodialysis, this proposed blood stream adjuster cannot be fitted in the artificial blood vessel simply.

SUMMARY OF THE INVENTION

It is an object of the invention to provide a hemodialysis use adjunctive device improved so that the blood flow can be increased when the hemodialysis is performed and can be reduced except when the hemodialysis is performed, whereby while hemodialysis can be performed properly, internal membrane thickening of the vein and the resulting stricture or obstruction of the same can be prevented.

In order to accomplish the above-said object, the present invention provides improvement for a hemodialysis use adjunctive device which comprises an artificial blood vessel to be transplanted in the body at a location between an artery and a vein, a T-shaped tubular body comprising a straight tube portion and a stem portion and interposed in the artificial blood vessel, and an access tube provided at one end thereof with a jack having a pair of needles and is used for hemodialysis by performing the step that the tubular body is transplanted in the body together with the artificial blood vessel in the state of the stem portion being exposed at its top end portion from the body and then, at the time of hemodialysis, the jack of the access tube is connected to the stem portion of the tubular body and the other end portion of the access tube is connected to a hemodialysis machine, for the hemodialysis. In the improved hemodialysis use adjunctive device, a throttling unit for reducing an area of a passage of the straight tube portion of the tubular body is provided in an interior of the straight tube portion of the tubular body and is arranged so that it can be located between the pair of needles of the jack projecting from the stem portion to the interior of the straight tube portion when the jack of the access tube is connected to the stem portion of the tubular body.

This arrangement can provide the result that when the artificial blood vessel and the tubular body, serving as the hemodialysis use adjunctive device, are transplanted in the human body and then, at the time of hemodialysis, the jack provided at one end portion of the access tube is connected to the top end portion of the stem portion of the tubular body exposed from the body and also the other end portion of the access tube is connected to the hemodialysis machine, for the hemodialysis, the throttling unit fitted in the straight tube portion of the tubular body is located between the pair of needles of the jack projecting from the stem portion of the tubular body to the interior of the straight tube portion so that the blood is drawn from the needle located on the artery side and returned from the needle located on the vein side. This can provide the result that the blood flow flowing through the interior of the adjunctive device and the hemodialysis machine during the hemodialysis can be increased to an extent corresponding to the order of 60-600 ml/min, without being affected by the throttling unit, and as a result, the hemodialysis can be performed safely. On the other hand, since the area of the passage of the straight tube portion of the tubular body is narrowed by the throttling unit fitted in the straight tube portion of the tubular body, the blood flow flowing through the artificial blood vessel and the tubular body of the adjunctive device transplanted in the body is reduced and thus the hydrodynamic stress acting on the blood vessel wall is reduced except when the hemodialysis is performed. As a result of this, the internal membrane thickening of the vein and the resulting stricture or obstruction of the same can be prevented.

BRIEF DESCRIPTION OF THE DRAWINGS

The above and other objects and advantages of the present invention will be clarified further from reading of the following detailed description and accompanying drawings, in which.

DETAILED DESCRIPTION OF THE PREFERRED EMBODIMENTS

In the following, an embodiment of the present invention will be described in detail with reference to the accompanying drawings.

Figure 1:
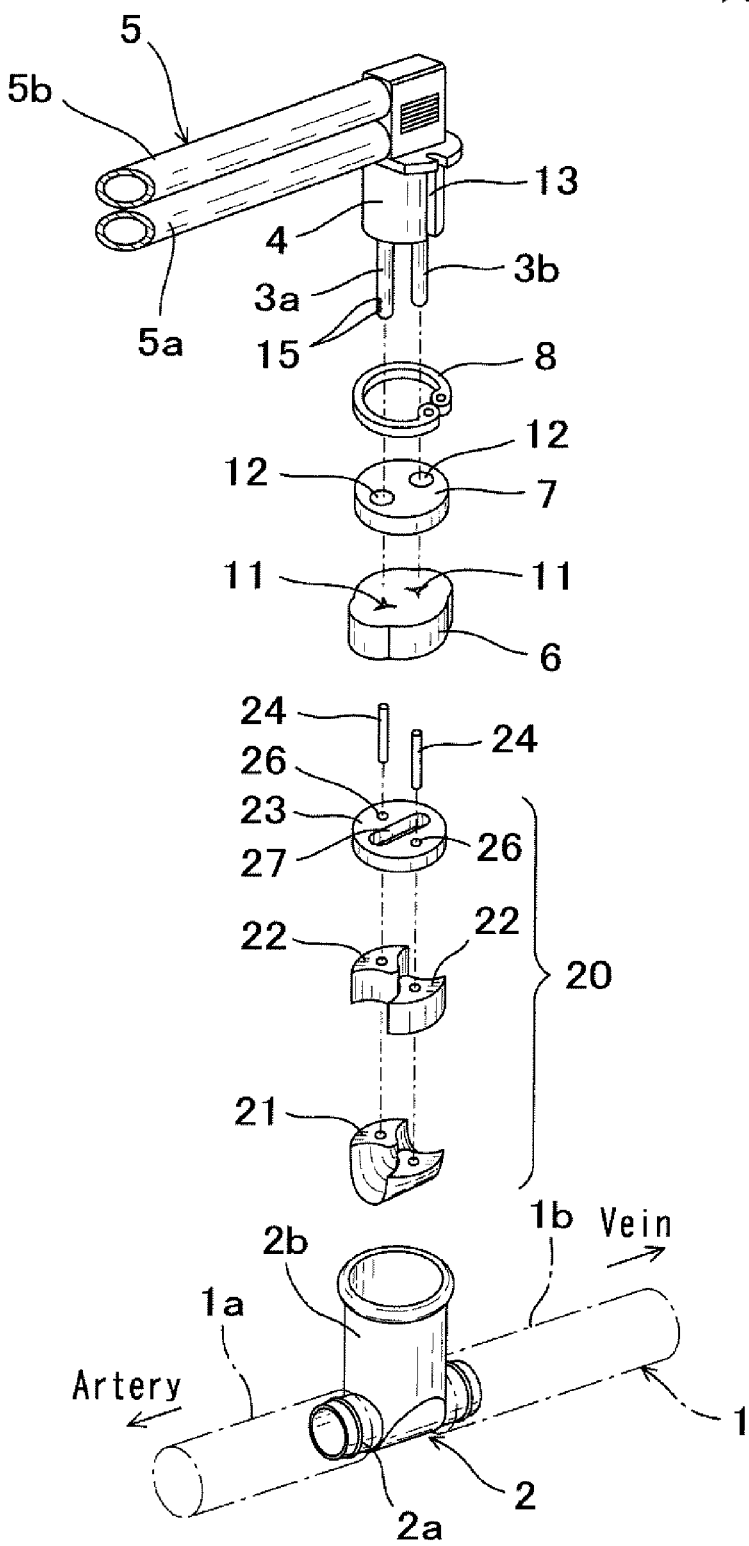
FIG. 1 is an exploded perspective view of a hemodialysis use adjunctive device according to an embodiment of the present invention.

FIG. 1 shows the entire structure of a hemodialysis use adjunctive device A according to an embodiment of the present invention. This adjunctive device A comprises an artificial blood vessel 1 formed of a flexible synthetic resin, a tubular body 2 interposed in the artificial blood vessel 1, and an access tube 5 provided at one end portion thereof with a jack 4 having a pair of needles 3a, 3b.

The tubular body 2 is in T shape comprising a straight tube portion 2a and a stem portion 2b, and an end portion 1a of the artificial blood vessel 1 on the artery side and an end portion 1b of the artificial blood vessel 1 on the vein side are connected to opposite ends of the straight tube portion 2a, respectively. In surgical operation of transplantation, the tubular body 2 is transplanted in an upper arm of a patient together with the artificial blood vessel 1 in the state of the stem portion 2b being exposed at its top end portion from his/her upper arm. The artificial blood vessel 1 is transplanted in between the brachial artery and the brachial vein. At the time of hemodialysis, the jack 4 of the access tube 5 is connected to the stem portion 2b of the tubular body 2 and the other end portion of the access tube 5 is connected to a hemodialysis machine (not shown), for the hemodialysis.

Figure 2:
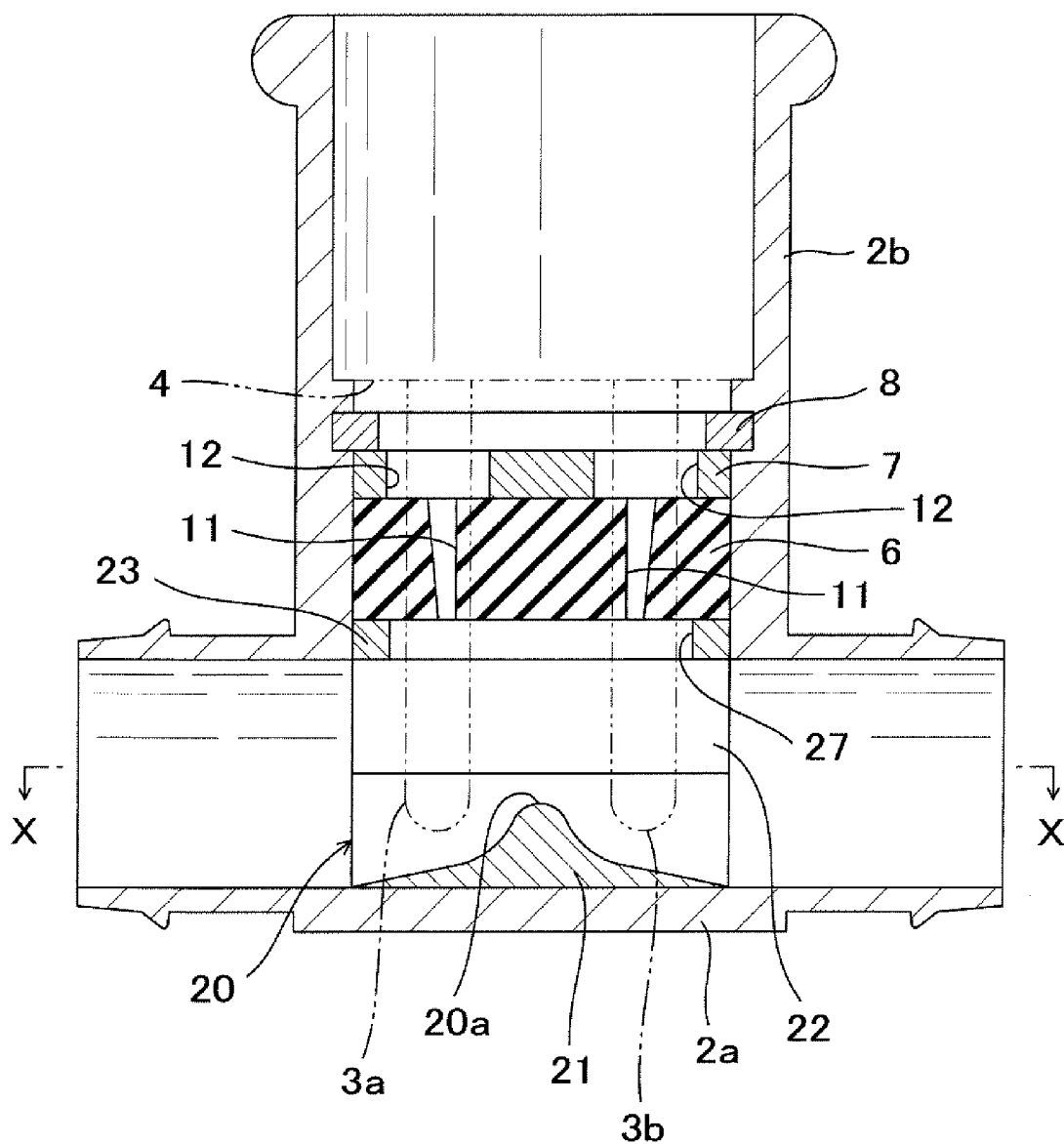
FIG. 2 is a vertical cross-sectional view of a tubular body of the hemodialysis use adjunctive device.
Figure 3:
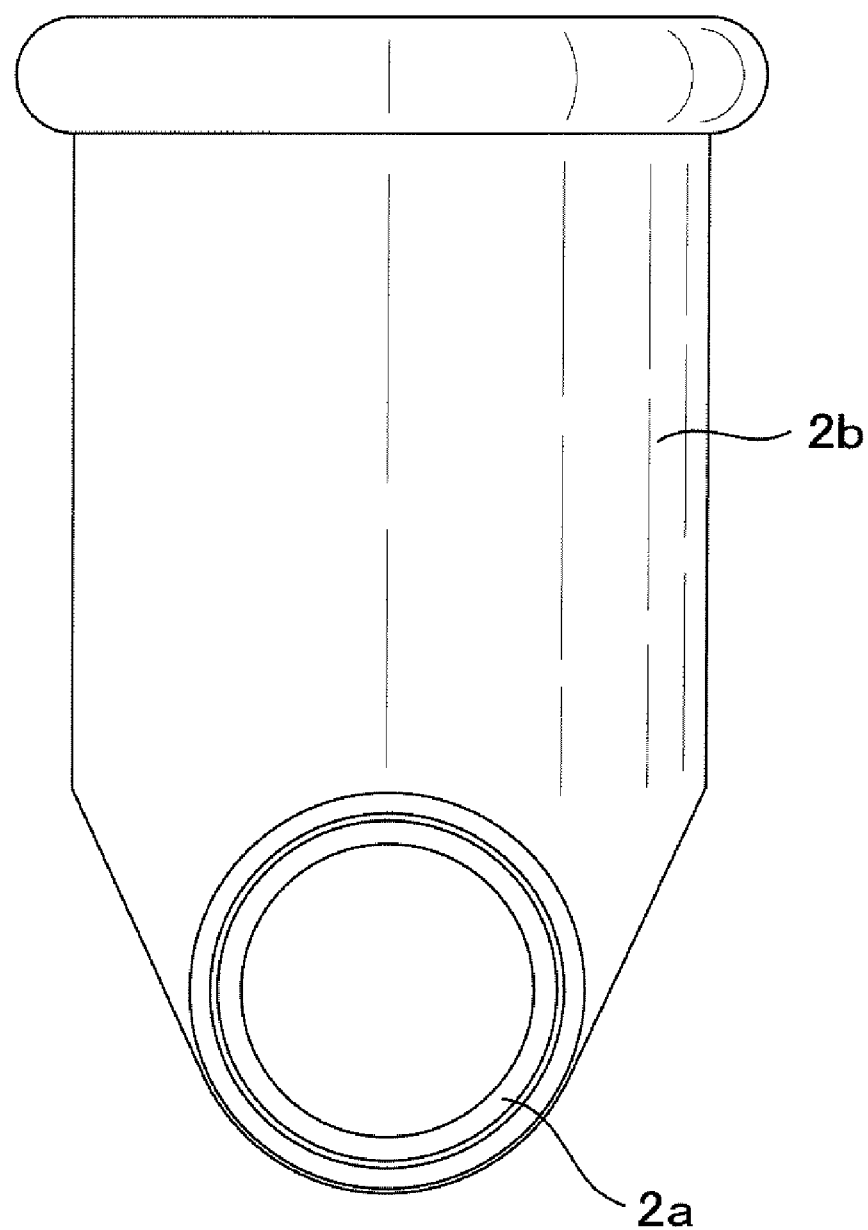
FIG. 3 is a side elevation view of the same.
Figure 4:
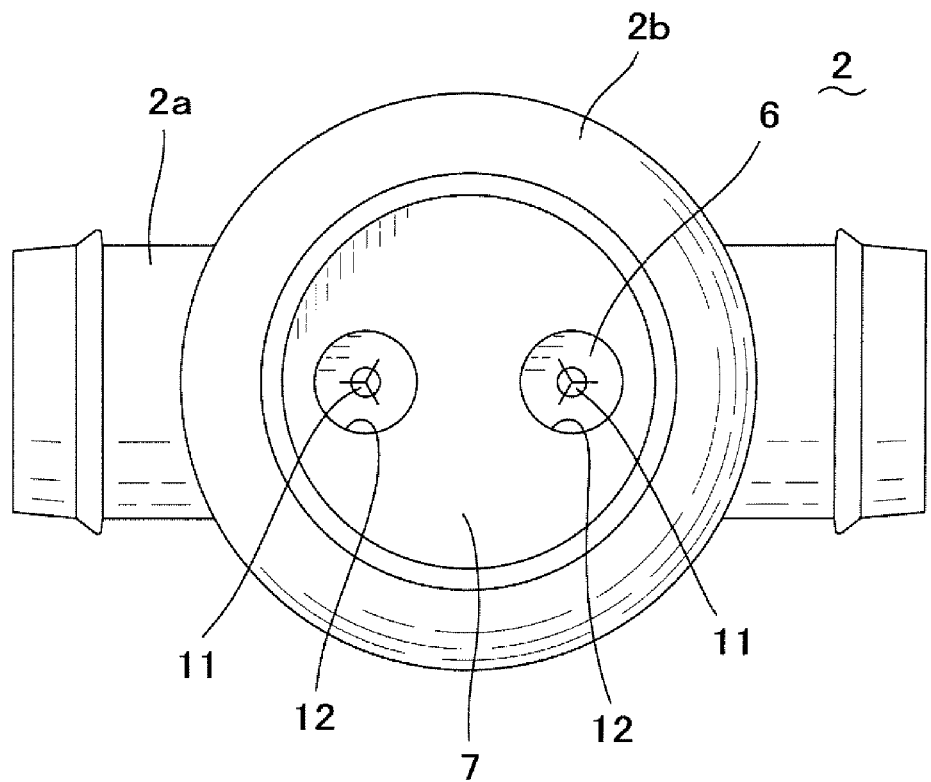
FIG. 4 is a plan view of the same.

As shown in enlargement and in detail in FIG. 2 and FIG. 4, the stem portion 2b of the tubular body 2 is in generally tube form communicating with the straight tube portion 2a. In the stem portion 2b, a septum 6 formed of elastic rubber or synthetic resin and a pressure-proof metal plate 7 abutted on an upper surface of the septum 6 are fitted and retained by means of a stop ring 8. Each of the septum 6 and the pressure-proof plate 7 has a pair of insertion holes 11, 11/12, 12, corresponding to the pair of needles 3a, 3b of the jack 4 of the access tube 5. When the jack 4 of the access tube 5 is connected to the stem portion 2b of the tubular body 2, the insertion holes 11 of the septum 6 are opened to permit the corresponding needles 3a, 3b of the jack 4 to pass through them, while on the other hand, when not connected thereto, the insertion holes 11 are closed in liquid-tight relation. A sealing material, not shown, is fitted around an outside of the septum 6 to keep liquid-tight between the outside of the septum 6 and an inside wall of the stem portion 2b.

On the other hand, the access tube 5 has a blood collection tube 5a communicating with the one needle 3a of the jack 4 and a blood return tube 5b communicating with the other needle 3b of the jack 4. The blood collection tube 5a and the blood return tube 5b are color-coded entirely or partly at joint portions thereof to the hemodialysis machine, in order to prevent wrong connection to the hemodialysis machine. For example, the blood collection tube 5a and the blood return tube 5b are separated from each other by red and blue, respectively. The jack 4 of the access tube 5 has a positioning groove 13 formed in an outside surface thereof to extend longitudinally of the needles 3a, 3b. A fitting structure is formed by the positioning groove 13 and a cooperative projection (not shown) provided at the stem portion 2b of the tubular body 2, to permit the jack 4 of the access tube 5 to fit in the stem portion 2b of the tubular body 2 only when the jack 4 is put in the proper position with respect to the stem portion 2b. As shown in FIG. 2, when the jack 4 is set in the proper position with respect to the stem portion 2b, the one needle 3a of the jack 4 communicating with the blood collection tube 5a of the access tube 5 extends from the stem portion 2b into the straight tube portion 2a to a location to the artery side and the other needle 3b of the jack 4 communicating with the blood return tube 5b of the access tube 5 extends from the stem portion 2b into the straight tube portion 2a to a location to the vein side. The needles 3a, 3b of the jack 4 have, at tip end portions thereof, a plurality of small, outward-looking holes 15, 15 (two holes are depicted in the drawing) formed in a back-to-back relation, as shown in FIG. 1.

Figure 5:
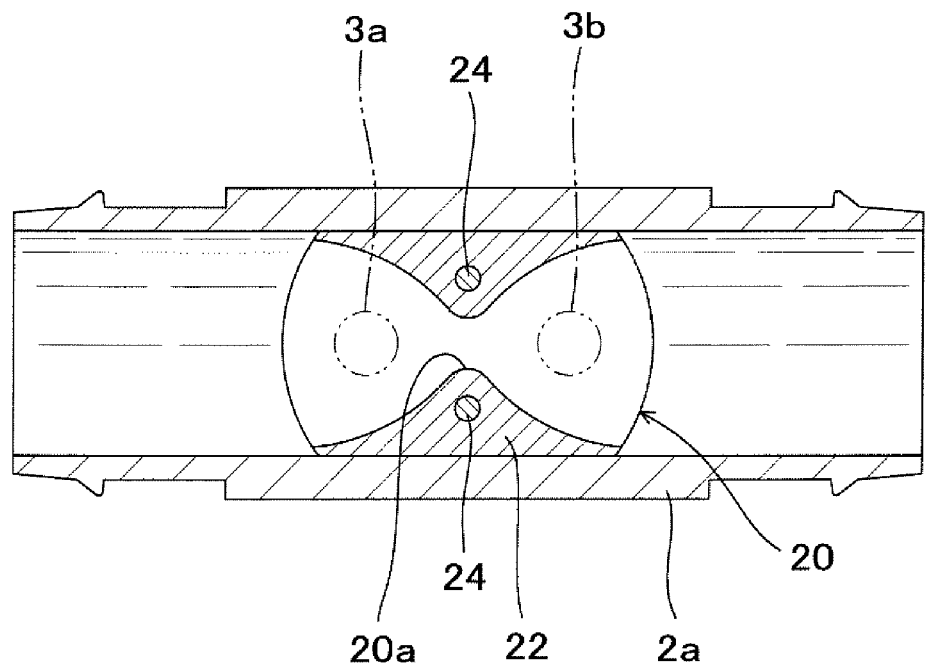
FIG. 5 is a sectional view taken along line X-X of FIG. 1.

As shown in FIG. 5 as well as FIGS. 1 and 2, a throttling unit 20 for reducing an area of a passage of the straight tube portion 2a is provided in an interior of the straight tube portion 2a of the tubular body 2, which is cited as a characteristic feature of the invention. This throttling unit 20 is formed to extend in an axial direction of the straight tube portion 2a to an extent substantially equal to an inner diameter of the stem portion 2b and has a throttle center 20a which is located at an axial center of the straight tube portion 2a and is arranged to be located between the pair of needles 3a, 3b of the jack 4 projecting from the stem portion 2b to the interior of the straight tube portion 2a when the jack 4 of the access tube 5 is connected to the stem portion 2b of the tubular body 2. An area of a passage at the throttle center 20a of the throttling unit 20 is set so that a shearing stress on a blood vessel wall of the brachial vein caused by the blood flow flowing through the artificial blood vessel 1 on the vein side 1b can be set to be not more than 2.0 dyne/cm$^2$.

The throttling unit 20 comprises a bottom plate 21 abutted on an inner wall of a lower half of the straight tube portion 2a to form a lower half of the throttling unit 20, two intermediate plates 22, 22 abutted on the bottom plate 21 to form an upper half of the throttling unit 20, a top plate 23 abutted on the intermediate plates 22, 22 and fitted in the stem portion 2b, and two coupling pins 24, 24 for coupling these three elements 21-23 together to form a unit. The throttling unit 20 is constructed so that it can be prevented from moving in an axial direction of the straight tube portion 2a by the top plate 23 being fitted in the stem portion 2b and also can be taken out through the stem portion 2b, for replacement, after removal of the septum 6 and the pressure-proof plate 7. The top plate 23 has two pin holes 26, 26 for allowing the respective coupling pins 24 to extend therethrough and a slot 27 formed between the both pin holes 26, 26, so that when the jack 4 of the access tube 5 is connected to the stem portion 2b of the tubular body 2, the pair of needles 3a, 3a of the jack 4 can extend to the interior of the straight tube portion 2a through the slot 27.

Then, the operation and effect of the illustrated embodiment will be described. When the artificial blood vessel 1 and the tubular body 2 of the hemodialysis use adjunctive device A are transplanted in the human body and then, at the time of hemodialysis, the jack 4 of the access tube 5 is connected to the top portion of the stem portion 2b of the tubular body 2 exposed from the human body and also the other end portion of the access tube 5 is connected to the hemodialysis machine, for the hemodialysis, the throttling center 20a of the throttling unit 20 fitted in the straight tube portion 2a of the tubular body 2 is located between the pair of needles 3a, 3b of the jack 4 projecting from the stem portion 2b of the tubular body 2 to the interior of the straight tube portion 2a so that the blood is drawn from the needle 3a located on the artery side and returned from the needle 3b located on the vein side. This can provide the result that the blood flow flowing through the interior of the adjunctive device A and the hemodialysis machine during the hemodialysis can be increased to an extent corresponding to the order of 60-600 ml/min, without being affected by the throttling unit 20, and as a result, the hemodialysis can be performed safely.

On the other hand, since the area of the passage is narrowed by the throttling unit 20 fitted in the straight tube portion 2a of the tubular body 2, the blood flow flowing through the artificial blood vessel 1 and tubular body 2 of the adjunctive device A is reduced and thus the hydrodynamic stress acting on the blood vessel wall of the brachial vein in which the artificial blood vessel 1 is transplanted is reduced except when the hemodialysis is performed. As a result of this, the internal membrane thickening of the brachial vein and the resulting stricture or obstruction of the same can be prevented. In the illustrated embodiment, in particular, since the shearing stress acting on the blood vessel wall of the brachial vein caused by the throttling unit 20 is set to be not more than 2.0 dyne/cm², occurrence of the internal membrane thickening of the brachial vein and the resulting stricture or obstruction of the same can surely be prevented.

In addition, since the throttling unit 20 is fitted in the tubular body 2 in the replaceable manner through the stem portion 2b of the tubular body 2, the throttling unit 20 can be replaced at regular intervals before deterioration is caused by being exposed to the blood flow. This can provide the advantage that the adjunctive device A can be kept longer with its function kept in the good condition, thus contributing to prolongation of the durable term.

While a preferred embodiment of the present invention has been illustrated and described above, the present invention covers various modifications without being limited to the embodiment described above. For example, while in the above-described embodiment, the throttling unit 20 is fitted in the straight tube portion 2a of the tubular body 2 in such a manner as to be replaced through the stem portion 2b of the tubular body 2, the present invention may be modified so that the throttling unit 20 may be formed integrally with the tubular body 2 or may be assembled in the tubular body 2 in a non-replaceable manner, if required.

Also, while in the above-described embodiment, the throttling unit 20 comprises the three elements of the bottom plate 21, the intermediate plates 22, and the top plate 23, the present invention may be modified so that the throttling unit 20 may be formed by a single element or two elements.

What is claimed is:

1. A hemodialysis use adjunctive device comprising:
    an artificial blood vessel being transplanted in the body at a location between an artery and a vein,
    a T-shaped tubular body having a straight tube portion and a stem portion, the T-shaped tubular body being interposed in the artificial blood vessel, wherein the straight tube portion is for communicating between a portion of the artificial blood vessel on the artery side and a portion of the same on the vein side, and the stem portion is integrally formed with the straight tube portion so that it can orthogonally communicate with the straight tube portion at one end thereof at an intermediate portion of the straight tube portion,
    an access tube provided at one end thereof with a jack having a pair of needles, wherein the hemodialysis use adjunctive device is used in hemodialysis wherein the tubular body is transplanted in the body together with the artificial blood vessel in the state of the stem portion being exposed at its top end portion from the body and, at the time of hemodialysis, the jack of the access tube is connected to the stem portion of the tubular body and the other end portion of the access tube is connected to a hemodialysis machine, and
    restriction unit reducing an area of the straight tube portion of the tubular body, the restriction unit is provided in an interior of the straight tube portion of the tubular body, and the restriction unit includes a flow-restricting center located between the pair of needles of the jack projecting from the stem portion to the interior of the straight tube portion when the jack of the access tube is connected to the stem portion of the tubular body, and
    the restriction unit controlling the blood flow resulting in a shearing stress on a blood vessel wall of the vein caused by the blood flow flowing through the artificial blood vessel on the vein side of not more than 2.0 dyne/cm².

2. The hemodialysis use adjunctive device according to claim 1, wherein the restriction unit is replaceable through the stem portion of the tubular body.

3. The hemodialysis use adjunctive device according to claim 1, wherein the restriction unit is formed to extend in an axial direction of the straight tube portion to an extent substantially equal to an inner diameter of the stem portion.

4. The hemodialysis use adjunctive device according to claim 3, wherein the flow-restricting center is an area at which a percentage of reduction of area is highest.

5. The hemodialysis use adjunctive device according to claim 4, wherein the flow-restricting center is located at an axial center at an axial center of the straight tube portion and is located between the pair of needles of the jack projecting from the stem portion to the interior of the straight tube portion when the jack of the access tube is connected to the stem portion of the tubular body.

6. The hemodialysis use adjunctive device according to claim 3, wherein the restriction unit comprises a bottom plate abutted on an inner wall of a lower half of the straight tube portion to form a lower half of the restriction unit, two intermediate plates abutted on the bottom plate to form an upper half of the restriction unit, a top plate abutted on the intermediate plates and fitted in the stem portion, and two coupling pins for coupling the above-said three elements together to form a unit.

7. The hemodialysis use adjunctive device according to claim 6, wherein the restriction unit is prevented from moving in an axial direction of the straight tube portion by the top plate being fitted in the stem portion and also being taken out through the stem portion, for replacement.

8. The hemodialysis use adjunctive device according to claim 7, wherein the top plate has two pin holes to allow the respective coupling pins to extend therethrough, and a slot formed between the both pin holes, so that when the jack of the access tube is connected to the stem portion of the tubular body, the pair of needles of the jack is able to the interior of the straight tube portion through the slot.

* * * * *